(12) United States Patent
Fujii

(10) Patent No.: US 6,613,071 B1
(45) Date of Patent: *Sep. 2, 2003

(54) WHOLE BODY THERMOTHERAPY TREATMENT APPARATUS

(75) Inventor: Yoshiya Fujii, Osaka (JP)

(73) Assignee: Sun Medical Co., Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 09/610,515

(22) Filed: Jul. 6, 2000

(51) Int. Cl.⁷ .................................................. A61N 1/00
(52) U.S. Cl. ...................................................... 607/91
(58) Field of Search ............................ 607/91, 90, 92, 607/100, 95, 94, 93, 88; 128/205.26; 600/21

(56) References Cited

U.S. PATENT DOCUMENTS

| 3,741,218 A |   | 6/1973  | Novak         |           |
|-------------|---|---------|---------------|-----------|
| 3,902,488 A |   | 9/1975  | Sheppard      |           |
| 4,100,415 A | * | 7/1978  | Blaisdell et al. | 250/455.11 |
| 4,469,102 A | * | 9/1984  | Fish          | 250/494.1 |
| 4,683,887 A | * | 8/1987  | Kramer et al. | 362/218   |
| 4,825,868 A | * | 5/1989  | Susa et al.   | 219/217   |
| 4,884,574 A |   | 12/1989 | Hardie et al. |           |
| 4,976,706 A |   | 12/1990 | Aki et al.    |           |
| 5,304,213 A |   | 4/1994  | Berke et al.  |           |
| 5,645,578 A |   | 7/1997  | Daffer et al. |           |
| 5,776,048 A | * | 7/1998  | Jo            | 600/21    |
| 5,891,186 A | * | 4/1999  | Daffer et al. | 600/21    |
| 6,004,344 A |   | 12/1999 | Fujii         |           |

FOREIGN PATENT DOCUMENTS

| CN | 331146  | 5/1998 |
| CN | 386439  | 4/2000 |
| FR | 779941  | 4/1935 |
| FR | 1005211 | 4/1952 |

* cited by examiner

Primary Examiner—Linda C. M. Dvorak
Assistant Examiner—Kenneth Schopfer
(74) Attorney, Agent, or Firm—Fulbright & Jaworski L.L.P.

(57) ABSTRACT

A thermotherapy treatment apparatus includes a human body mounting portion, a cover portion for covering a human body corresponding site on the human body mounting portion, a far infrared ray radiation source for radiating far infrared rays onto the human body corresponding site, a ventilation hole for ventilating the human body corresponding site, and a ventilation duct which is in communication with the ventilation hole.

18 Claims, 3 Drawing Sheets

WHOLE BODY THERMOTHERAPY TREATMENT APPARATUS

BACKGROUND OF THE INVENTION

1. Field of the Invention

The present invention relates to a whole body thermotherapy treatment apparatus, and more particularly to a whole body thermotherapy treatment apparatus for raising the body surface temperature and deep intracorporeal temperature, promoting blood circulation, and alleviating the stiffness, pains, and numbness caused by diseases in various parts of the body as well as treating various diseases, malignant tumors, and viral diseases by radiating far infrared rays to a human body

2. Description of the Related Art

Hitherto, for malignant tumors such as cancers, sarcoma, etc., treatments such as abscission by operations, radiation of radioactive rays, administration of drugs, etc., have been given, but tumors which have metastasized are difficult to treat. Even if they are at the initial stages, operations and other methods may cause excessively heavy burdens to the human body, lower the immunological competence, and have problems of recurrence of tumors, occurrence of other diseases, etc. Viral diseases cannot be treated unless suitable vaccine is present, and such is the state of the art that there is no effective treatment when people are infected with AIDS virus, etc.

Because it has been found out in recent years that cells of such malignant tumors and viruses die out or are inactivated when heated to temperatures exceeding 41° C., thermotherapy has attracted keen attention, and treatments for immersing patients in warm water or methods for radiating infrared rays have been developed, and infrared ray radiation apparatus have started to be fabricated.

However, since the treatment by immersing patients in warm water is achieved by thermal conduction from the human body surface, long time is required for heating the inside of the human body, imposing a heavy burden on the human body. In addition, the infrared ray radiation sources used for infrared ray radiation apparatus which have been fabricated and commercially available to date are said to be far infrared, ray radiation sources, but in actuality contain a large quantity of near infrared rays, and has a construction in which the infrared ray radiation source is formed in a single unit. Near infrared rays have large energy, and provide low permeability to a human body, and require a long time to heat the depth of the human body, and patients must be anesthetized for treatment in order to prevent patients from moving. In addition, because the human body is exposed to the infrared ray radiation source containing near infrared rays for a long time, the energy applied to the human body surface increases, and a problem of low-temperature burns occurs in the patients, and in order to reduce this problem, an expensive control means must be provided.

In view of the aforesaid problems in the prior art, the inventors of the present invention have invented a far infrared ray radiation apparatus that can allow far infrared rays to reach the depth of the human body in a short time without causing low-temperature bus in the patients (See U.S. Pat. No. 6,004,344).

SUMMARY OF THE INVENTION

Further, the inventors of the present invention have made efforts in order to improve a thermotherapy treatment apparatus using the aforesaid infrared ray radiation apparatus, and completed an invention of a thermotherapy treatment apparatus capable of allowing far infrared rays to reach the depth of the human body in a short time and setting the radiation intensity arbitrarily for each part of the human body as well as maintaining the human body atmosphere in the optimal state, increasing the treatment effects, and maintaining the chamber environment in a good condition without causing low-temperature burns in the human body.

Namely, the construction of a thermotherapy treatment apparatus according to the present invention is a thermotherapy treatment apparatus including a human body mounting portion; a cover portion for covering a human body corresponding site on the human body mounting portion; a far infrared ray radiation source for radiating far infrared rays onto the human body corresponding site, the far infrared rays being capable of raising a temperature of a depth portion thereof, and a ventilation hole for ventilating the human body corresponding site, characterized in that a ventilation duct is provided which is in communication with the ventilation hole.

According to this construction, since the ventilation duct being in communication with the ventilation hole is provided, it is possible to prevent the human body atmosphere inside the cover portion from directly entering a chamber if an end portion of the ventilation duct on the side opposite to the other end portion that is in communication with the ventilation hole is allowed to be in communication with the outside of the chamber or a processing device.

As a result, a good thermotherapy can be carried out by maintaining the human body atmosphere in an optimal state by ventilation, and also aggravation in terms of temperature, humidity, and odor of the environment inside the chamber can be prevented. Furthermore, even if a plurality of the thermotherapy treatment apparatus are disposed in the chamber, the environment inside the chamber is not aggravated.

It is preferable that a plurality of the ventilation holes are dispersed and arranged, and one common ventilation duct is provided for the plurality of ventilation holes.

According to this construction, since the plurality of ventilation holes are dispersed and arranged for ventilating each site in the human body atmosphere, the whole human body atmosphere can be made uniform more easily as compared with, for example, a case in which only one ventilation hole is provided for ventilation.

Furthermore, since one common ventilation duct is provided for the plurality of dispersed and arranged ventilation holes so as to assemble air for ventilation, the exhaust air discharged from the plurality of ventilation holes can be collectively carried out.

As a result of this, the whole human body atmosphere can be made uniform and the thermotherapy treatment effects can be enhanced more. In addition, the ventilation process can be carried out more rationally.

It is preferable that the ventilation hole is provided with a ventilation fan.

According to this construction, since a ventilation fan is disposed in each ventilation hole, the amount of ventilation in each ventilation hole can be adjusted, so that the whole human atmosphere can be made uniform all the more easily.

As a result of this, the thermotherapy treatment effects can be enhanced more.

Here, the ventilation fan may be disposed in all of the ventilation holes or may be disposed in some of the ventilation holes.

BRIEF DESCRIPTION OF THE DRAWINGS

The above and further objects, advantages, features, and aspects of the invention will be more fully apparent from the following detailed description with the accompanying drawings, in which.

DETAILED DESCRIPTION OF THE PREFERRED EMBODIMENTS

An embodiment of a thermotherapy treatment apparatus according to the present invention will be described in detail with reference to the drawings.

Figure 1:
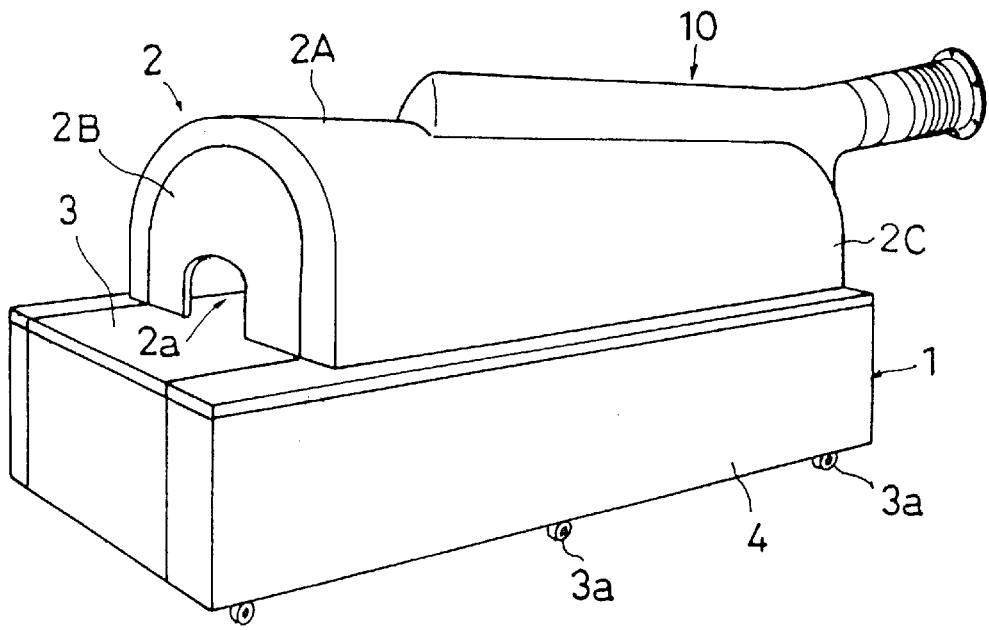
FIG. 1 is a perspective view illustrating one embodiment of a thermotherapy treatment apparatus according to the present invention.
Figure 2:
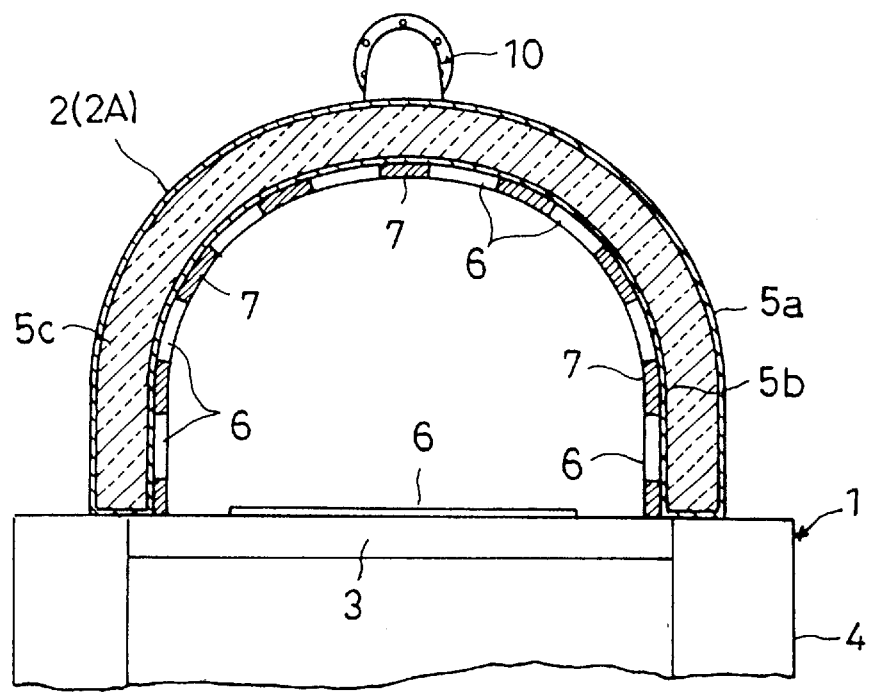
FIG. 2 is a vertical cross-sectional front view of the thermotherapy treatment apparatus of FIG. 1.
Figure 3:
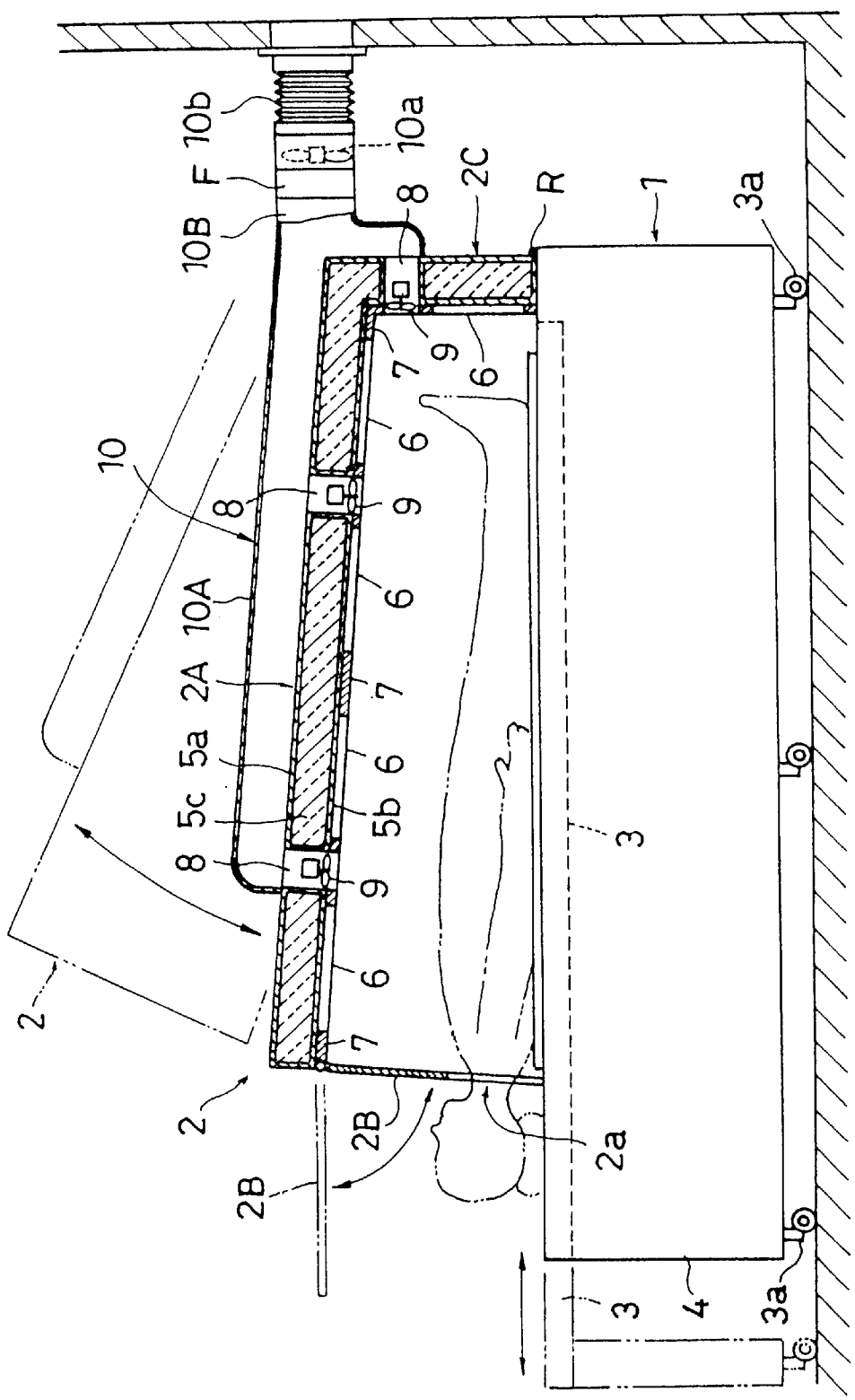
FIG. 3 is a vertical cross-sectional side view of the thermotherapy treatment apparatus of FIG. 1.
Figure 4:
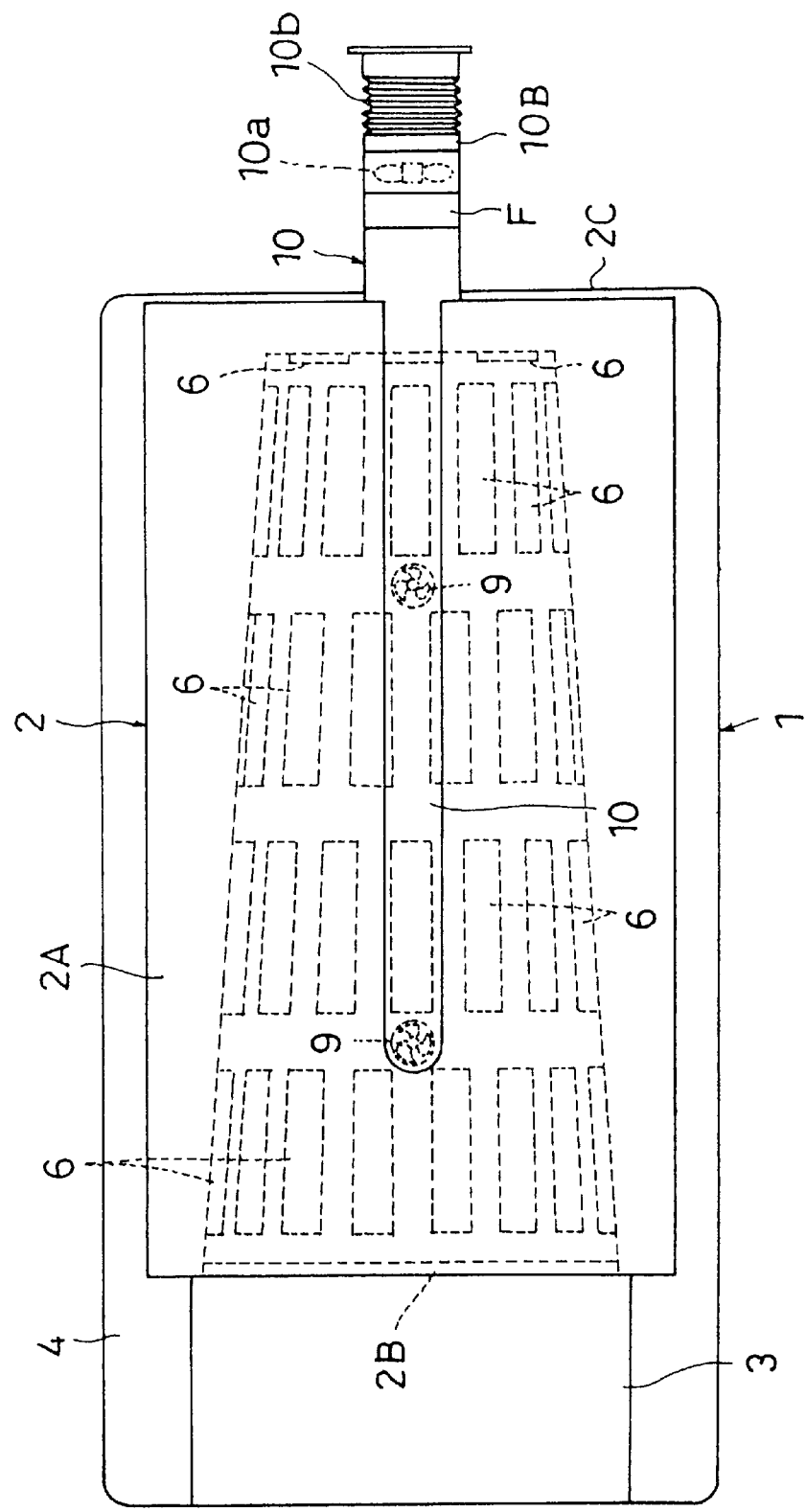
FIG. 4 is a plan view of the thermotherapy treatment apparatus of FIG. 1.

Referring to FIG. 1, this thermotherapy treatment apparatus is comprised of a bed portion 1 and a cover portion 2, and includes a heating means and a ventilating means. Referring to FIGS. 2 to 4, the bed portion 1 is comprised of a human body mounting portion 3 and a base portion 4 for accommodating the human body mounting portion 3 in a freely drawable manner. The human body mounting portion 3 includes caster wheels 3a attached thereto for facilitating the operation of letting the human body mounting portion in and out relative to the base portion 4. The base portion 4 can accommodate a power supply portion, a control portion, a device for measuring and displaying the condition of a patient, an oxygen supplying device, and others therein.

The cover portion 2 serves to cover a human body corresponding site on the human body mounting portion 3, and is mounted to the base portion 4 so as to allow a free opening and closing pivotal operation in an up-and-down direction with respect to a fulcrum R at the end of the foot side so that the accommodation of the patient, diagnosis, and disposal of the sensors and others can be carried out. The means for allowing the opening and closing pivotal operation may be, for example, a means for opening and closing with a human power or a means for opening and closing with a hydraulic actuator (hydraulic cylinder or hydraulic motor) or an electromotive actuator (electromotive motor or electromotive cylinder), and any of these means may be adopted.

Referring also to FIGS. 2 to 4, the cover portion 2 is comprised of a substantially semi-cylindrical cover main body 2A, a head portion shielding cover 2B for closing an opening of a head side of the cover main body 2A in such a manner that a human body neck portion insertion inlet 2a remains, and a foot portion shielding cover 2C for closing an opening of a foot side of the cover main body 2A. The cover main body 2A and the foot portion shielding cover 2C are integrally formed. The cover main body 2A and the foot portion shielding cover 2C have a three-layer structure in which a heat-insulating material 5c is sandwiched between an outer panel 5a and an inner surface panel 5b. The head portion shielding cover 2B is mounted to the cover main body 2A so as to allow free opening and closing pivotal operation so that the human body can enter or exit without pivotally releasing the cover main body 2A. It is preferable that the whole or a part of the head portion shielding cover 2B is made of a transparent member so as to allow a function as a window for looking into the inside.

The heating means is a means for heating the inside of the human body lying on the human body mounting portion 3 by radiating far infrared rays that do not contain near infrared rays having a wavelength of less than 4 μm, to a human body corresponding site on the human body mounting portion 3. Referring to FIGS. 2 to 4, a far infrared ray radiation source 6 for radiating far infrared rays having a wavelength of 5 to 20 μm, preferably 8 to 15 μm, is attached to the inner surfaces of the cover main body 2A, the foot portion shielding cover 2C, and the human body mounting portion 3. Further, a reflection member 7 is attached to a part of the inner surfaces of the cover main body 2A and the foot portion shielding cover 2C where the far infrared ray radiation source 6 is not attached. More specifically, the site corresponding to a breast portion, the site corresponding to an abdomen portion, the site corresponding to an upper leg portion, and the site corresponding to a lower leg portion in the cover main body 2A are each provided with a plurality of far infrared ray radiation sources 6 dispersed and arranged in a circumferential direction. The foot portion shielding cover 2C is provided with a plurality of far infrared ray radiation sources 6 dispersed and arranged in a right-and-left direction. The human body mounting portion 3 is provided with one far infrared ray radiation source 6 having a size such that the far infrared rays can be radiated to an entire portion of the human body except above the neck of the human body. Here, it is preferable that the far infrared ray radiation sources 6 at each site can independently adjust the amount of far infrared ray radiation.

The far infrared ray radiation source 6 is made of a heater member that is heated by energization and an inorganic-system member that covers the surface thereof. The inorganic-system member is preferably made of ceramics such as zirconia-system or alumina-system and blocks the near infrared rays having a wavelength of less than 4 μm in the infrared rays generated by the heater member, or converts them to far infrared rays. An electric power supply cord for the far infrared radiation source 6 disposed in the cover portion 2 is disposed in the inside of the heat-insulating material 5c. The ceramics in the inorganic-system member preferably have a thickness as large as possible in order to ensure blocking or conversion of the near infrared rays that are made liable to be generated by a temperature rise. With the use of such a far infrared ray radiation source 6, the temperature of a deep portion of the human body can be raised to produce the aforesaid treatment effects.

The reflection member 7 is preferably a member coated with aluminum, a stainless steel material, or various thin plates in order to efficiently reflect the far infrared rays. As illustrated in the drawings, the reflection member 7 is constructed with a member different from the inner surface panel 5b. Alternatively, however, the inner surface panel 5b may be formed of a reflecting material to allow the inner surface panel 5b to serve as the reflecting member 7 as well. In this case, the far infrared ray radiation source 6 is preferably mounted to the inner surface panel 5b via an insulation material or a heat-insulating material.

The ventilation means ventilates the human body atmosphere so that the whole human body atmosphere on the human body mounting portion 3 may have a temperature from 40 to 80° C., or an optimal temperature in accordance with the symptom and the treatment purpose. Referring to FIGS. 1, 3, and 4, the ventilation means is constructed by forming a plurality of ventilation holes 8 (two ventilation holes are illustrated in the drawings, but the number can be suitably changed) at the center in the circumferential direction of the cover main body 2A in the cover portion 2 with a spacing in the longitudinal direction, forming one ventilation hole 8 in the foot portion shielding cover 2C, disposing a ventilation fan 9 for forced ventilation in each ventilation hole 8, and disposing a ventilation duct 10 that includes an exhaust fan 10a and a filter F for assembling air discharged from each ventilation hole 8 and forcibly discharging the air to the outside of the chamber.

The ventilation fans 9 are preferably capable of independently adjusting the amount of ventilation. A substantially semi-cylindrical member that forms a passageway together with the upper surface of the outer panel 5a of the cover portion 2 is mounted to the outer panel 5a to construct a duct portion 10A of the ventilation duct 10 for assembling the exhaust gas. A duct portion 10B connected to the duct portion 10A guides the exhaust gas to the outside of the chamber and includes a bellows portion 10b disposed at a rear end position thereof. By the presence of this bellows portion 10b, the ventilation duct 10 pivots smoothly by following the opening and closing pivotal movement of the cover portion 2.

By adjusting the amount of ventilation from each ventilation hole 8 with the use of this ventilation means, the whole human body atmosphere can be easily adjusted to have a uniform temperature. Furthermore, the exhaust gas containing moisture, odor components, and others can be discharged to the outside of the chamber, so that the inside of the chamber is not contaminated with the exhaust gas, and the patients or the inhabitants in the chamber are not brought into an uncomfortable mood.

The thermotherapy treatment apparatus constructed as above is used in a state in which the head portion of the human body protrudes to the outside. Sensors needed for checking the body condition of the patient, such as the temperature of each part in the body, the blood pressure, and the pulse rate, can be mounted to the patient for performing a treatment. Further, when the far infrared rays are radiated, the radiation intensity is increased at an initial stage of the treatment so as to raise the intracorporeal temperature as soon as possible and then, after the temperature has reached a set level, the radiation is controlled to maintain the set level.

ANOTHER EMBODIMENTS OF THE INVENTION (a) In the above-described embodiment, a plurality of far infrared ray radiation sources 6 are dispersed and arranged. However, one large far infrared ray radiation source 6 may be disposed for carrying out the invention.

(b) In the above-described embodiment, an example is shown in which a plurality of ventilation holes 8 are disposed. However, the number, the forming position, the size, the shape, and others of the ventilation holes 8 can be suitably changed.

(c) In the above-described embodiment, an example is shown in which a ventilation fan 9 is disposed in the ventilation hole 8, and an exhaust fan 10a is disposed in the ventilation duct 10. However, it is possible to adopt a construction in which only the exhaust fan 9 is disposed in the ventilation hole 8, and a fan is not disposed in the ventilation duct 10. Alternatively, it is possible to adopt a construction in which only the ventilation duct 10 is provided with an exhaust fan and a fan is not disposed in the ventilation hole 8. In the latter case, it is preferable if a damper is provided in the ventilation hole 8 to make it possible to adjust the amount of ventilation, because then the whole human body atmosphere can be made uniform.

Needless to say, it is possible to adopt a construction in which the ventilation depends only on natural ventilation without disposing a fan.

(d) In the above-described embodiment, an example has been shown in which the cover main body 2A and the foot portion shielding cover 2C constituting the cover portion 2 are integrally formed so as to allow a free opening and closing pivotal operation in an up-and-down direction with respect to a fulcrum R at the end of the foot side. However, the cover portion 2 may be split into plural parts in the direction of the lying human body. In other words, it is possible to adopt a construction in which the cover portion 2 can be split into a breast portion, an abdomen portion, a leg portion, and others of the human being, and only the leg portion is pivotable with respect to a fulcrum at the end of the foot side, and the portions other than the leg portion can be opened and closed in a lateral direction with respect to fulcrums at the sides of the base portion.

(e) If sensors needed for checking the body condition of the patient, such as the temperature of each part in the body, the blood pressure, and the pulse rate, are mounted for performing the treatment, an opening and closing door capable of allowing the wiring connected to various measurement devices to be taken out can be disposed at one place or at plural places on the side surfaces of the cover portion 2. If the needed sensors are connected to each part of the patient through this opening and closing door, it is possible to prevent the wiring from being long and cumbersome with certainty, thereby providing an advantage that the work can be carried out easily and the convenience of the apparatus is increased.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

What is claimed is:

1. A thermotherapy treatment apparatus comprising:

a human body mounting portion;

a cover portion for covering a corresponding site of a human body on said human body mounting portion, and arranging a plurality of far-infrared ray radiation sources on the inner surface in a peripheral direction;

far-infrared ray radiation sources having an inorganic member that shields near-infrared rays with wavelengths of 4 $\mu$m or less or converts said near-infrared rays to far-infrared rays to radiate said far-infrared rays, said far-infrared ray radiation sources capable of raising a temperature of a depth portion of said corresponding site of the human body;

at least one ventilation hole for ventilating said corresponding site of the human body; and at least one ventilation duct in communication with said ventilation hole which discharges a human body atmosphere in said cover portion to an environment outside the room in which said human body mounting portion for mounting a human body is located, by bringing end portion on the opposite side to the end portion communicating with the ventilation hole into communication with an environment outside the room or with the treatment apparatus.

2. The thermotherapy treatment apparatus according to claim 1, wherein a plurality of said far-infrared radiation ray sources are provided and arranged in a peripheral direction at respective sites corresponding to the chest portion, abdomen portion, upper limb portions and lower limb portions of said human body of said cover portion.

3. The thermotherapy treatment apparatus according to claim 1, wherein a plurality of said far-infrared ray radiation sources are provided and arranged in a direction from left to right on a foot portion shielding cover closing an opening in a foot side of said cover portion.

4. The thermotherapy treatment apparatus according to claim 1, wherein a plurality of said far-infrared ray radiation sources and reflecting members are arranged in a peripheral direction on the inner surface of said cover portion.

5. The thermotherapy treatment apparatus according to claim 4, wherein said reflecting members are made of aluminum plates.

6. The thermotherapy treatment apparatus according to claim 4, wherein said far-infrared ray radiation sources and said reflecting members are alternately arranged in a peripheral direction.

7. The thermotherapy treatment apparatus according to claim 1, wherein said human body mounting portion can be housed in a freely drawable manner.

8. The thermotherapy treatment apparatus according to claim 1, wherein a head portion shielding cover for closing an opening of a head side of said cover portion in such a manner that a human body neck portion insertion inlet remains, is mounted to said cover main body in a freely opening and closing pivotal manner.

9. The thermotherapy treatment apparatus according to claim 1, wherein a plurality of said ventilation holes are arranged at respective sites corresponding to the abdomen portion and lower limb portions of the human body of said cover portion.

10. The thermotherapy treatment apparatus according to claim 1, said ventilation holes are arranged in said foot portion shielding cover.

11. The thermotherapy treatment apparatus according to claim 1, wherein a plurality of said ventilation holes are provided and arranged to communicate with a single ventilation duct.

12. The thermotherapy treatment apparatus according to claim 11, wherein a ventilation fan is operably provided in at least one of said ventilation holes.

13. The thermotherapy treatment apparatus according to claim 11, wherein said cover portion is formed substantially in a semi-cylindrical shape, and said ventilation hole is provided at least at a top portion of said cover portion, and said ventilation duct is in communication with the ventilation hole.

14. The thermotherapy treatment apparatus according to claim 1, further comprising an exhaust fan provided in said ventilation duct collecting air discharged from said ventilation holes to forcibly discharge the air to the external environment and a filter disposed on an upstream side of said exhaust fan.

15. The thermotherapy treatment apparatus according to claim 1, further comprising a bellows portion disposed at a rear end position of said ventilation duct which follows an opening and closing pivotal movement of said cover portion.

16. The thermotherapy treatment apparatus according to claim 14, further comprising a bellows portion disposed at a rear end position of said ventilation duct which follows an opening and closing pivotal movement of said cover portion.

17. The thermotherapy treatment apparatus according to claim 11, wherein said cover portion comprises a substantially semi-cylindrical cover main body;
 a head portion shielding cover for closing an opening of a head side of said cover main body in such a manner that a human body neck portion insertion inlet remains; and
 a foot portion shielding cover for closing an opening of a foot side cover main body.

18. The thermotherapy treatment apparatus according to claim 12, comprising a head portion shielding cover wherein said ventilation fan ventilates a human body atmosphere on said human body mounting portion so that a whole of said human body atmosphere may have a temperature in accordance with a symptom and a treatment purpose, and at least a portion of a head portion shielding cover is transparent.

* * * * *